(12) United States Patent
Docherty et al.

(10) Patent No.: US 8,170,685 B2
(45) Date of Patent: May 1, 2012

(54) RADIANT THERAPEUTIC HEATING APPARATUS

(75) Inventors: Francis G. Docherty, Calgary (CA); Wendy Docherty, Calgary (CA); John Crerar, Calgary (CA)

(73) Assignee: CT Investments Ltd., Calgary (CA)

( * ) Notice: Subject to any disclaimer, the term of this patent is extended or adjusted under 35 U.S.C. 154(b) by 1243 days.

(21) Appl. No.: 11/574,723

(22) PCT Filed: Sep. 1, 2005

(86) PCT No.: PCT/IB2005/002617
§ 371 (c)(1),
(2), (4) Date: Aug. 22, 2007

(87) PCT Pub. No.: WO2006/024938
PCT Pub. Date: Mar. 9, 2006

(65) Prior Publication Data
US 2008/0262393 A1 Oct. 23, 2008

Related U.S. Application Data

(63) Continuation-in-part of application No. 11/051,086, filed on Feb. 4, 2005, now Pat. No. 7,693,580, which is a continuation-in-part of application No. 10/934,158, filed on Sep. 3, 2004, now Pat. No. 7,783,361.

(51) Int. Cl.
*A61F 7/00* (2006.01)
(52) U.S. Cl. .......... 607/100; 219/211; 219/217; 607/96; 607/108
(58) Field of Classification Search .............. 607/88–91, 607/96–100; 219/527, 528
See application file for complete search history.

(56) References Cited

U.S. PATENT DOCUMENTS
2,850,009 A 9/1958 McElwee
(Continued)

FOREIGN PATENT DOCUMENTS
WO WO-99/62302 A1 12/1999

OTHER PUBLICATIONS

Extended European Search Report issued Jan. 22, 2010 for European Application No. 05783464.0.
(Continued)

*Primary Examiner* — Roy Gibson
(74) *Attorney, Agent, or Firm* — Venable LLP; Keith G. Haddaway; Devesh Srivastava

(57) ABSTRACT

A radiant therapeutic heating apparatus may include a radiant heat generating layer having a plane surface including an infrared radiator adapted to radiate heat evenly from its surface, a pair of flexible electrically insulating and radiation-permeable layers located adjacent and covering opposite sides of the layer, a thermal insulation layer disposed against and covering one of the electrically insulating layers, and a sealed radiation permeable envelope enclosing the heating apparatus. The flexible heat generating layer may include a fiberglass material impregnated with a resistive material, which material may provide a surface temperature, when current is conducted therethrough, of no greater than about 54 degrees Celsius. Current limiting thermostats may be provided to prevent energy and temperature spikes. A stiffening element may help protect the components, and may orient portions of a user's body (such as, e.g., but not limited to, the wrist for repetitive strain injuries) in a therapeutic position. The heating apparatus may be used on animals such as, e.g., but not limited to, mammals, including pets, humans, horses and/or other living beings and/or creatures. The apparatus may be oriented as a blanket, and may incorporate, e.g., a rheostat, high-low, analog, digital, or other power control switch. It may be used for warming kennels, for treating hypothermia, for relieving neck, shoulder and/or back pain. It may be used for pre- post- and during, operative care. It may be combined with other therapy such as, e.g., massage and/or vibration.

69 Claims, 6 Drawing Sheets

U.S. PATENT DOCUMENTS

| | | | |
|---|---|---|---|
| 2,949,108 | A | 8/1960 | Vecchio |
| 3,751,620 | A | 8/1973 | Yuasa et al. |
| 3,885,553 | A | 5/1975 | Vecchio |
| 4,186,294 | A | 1/1980 | Bender et al. |
| 4,221,954 | A | 9/1980 | Cohen |
| 4,334,541 | A | 6/1982 | Leist et al. |
| D273,517 | S | 4/1984 | Medlin et al. |
| 4,507,816 | A | 4/1985 | Smith, Jr. |
| D279,818 | S | 7/1985 | Douglas |
| 4,563,843 | A | 1/1986 | Grether et al. |
| 4,607,624 | A | 8/1986 | Jefferson |
| 4,700,054 | A | 10/1987 | Triplett et al. |
| 4,888,472 | A | 12/1989 | Stitz et al. |
| 5,074,285 | A | 12/1991 | Wright et al. |
| 5,151,578 | A | 9/1992 | Phillips et al. |
| 5,324,911 | A | 6/1994 | Cranston et al. |
| 5,371,340 | A | 12/1994 | Stanfield |
| 5,674,423 | A | 10/1997 | Wright, Sr. |
| 5,686,005 | A | 11/1997 | Wright, Sr. |
| 5,841,944 | A | 11/1998 | Hutchinson et al. |
| 5,977,517 | A * | 11/1999 | Grosjean ................ 219/211 |
| 6,006,136 | A | 12/1999 | Glucksman |
| 6,067,404 | A | 5/2000 | Wilkins et al. |
| 6,108,581 | A | 8/2000 | Jung et al. |
| 6,185,742 | B1 | 2/2001 | Doherty |
| 6,188,051 | B1 | 2/2001 | Kusek |
| 6,235,049 | B1 * | 5/2001 | Nazerian ................ 607/108 |
| 6,254,922 | B1 | 7/2001 | Reichelt et al. |
| 6,261,261 | B1 | 7/2001 | Gordon |
| 6,263,158 | B1 | 7/2001 | Rutherford |
| 6,294,758 | B1 | 9/2001 | Masao et al. |
| 6,297,481 | B1 | 10/2001 | Gordon |
| 6,329,638 | B1 | 12/2001 | Bloodworth |
| 6,366,802 | B1 * | 4/2002 | Haber et al. ................ 600/474 |
| 6,392,206 | B1 | 5/2002 | Von Arx et al. |
| 6,392,208 | B1 | 5/2002 | Arx |
| 6,432,344 | B1 | 8/2002 | Eckman et al. |
| 6,433,317 | B1 | 8/2002 | Arx et al. |
| 6,434,328 | B2 | 8/2002 | Rutherford |
| 6,510,346 | B2 | 1/2003 | Gordon |
| 6,516,229 | B1 | 2/2003 | Wey |
| 6,517,501 | B1 | 2/2003 | Slautterback |
| 6,519,835 | B1 | 2/2003 | Von Arx et al. |
| 6,539,171 | B2 | 3/2003 | VonArx et al. |
| 6,554,787 | B1 | 4/2003 | Griffin et al. |
| 6,664,512 | B2 | 12/2003 | Horey et al. |
| 6,674,423 | B2 | 1/2004 | Isozaki |
| 6,689,994 | B2 | 2/2004 | Reichelt et al. |
| 6,744,978 | B2 | 6/2004 | Tweedy et al. |
| 6,748,646 | B2 | 6/2004 | Von Arx et al. |
| 2002/0169398 | A1 | 11/2002 | Hancock |
| 2004/0143199 | A1 | 7/2004 | Cotterell-Grant et al. |

OTHER PUBLICATIONS

Machine Translation of WO99/62302 from the EPO website, accessed Jan. 27, 2010.

English Language Abstract of WO99/62302 from the EPO website, accessed Jan. 27, 2010.

Office Action issued Mar. 4, 2009 by the USPTO for U.S. Appl. No. 11/051,086.

Office Action issued Sep. 5, 2008 by the USPTO for U.S. Appl. No. 11/051,086.

Office Action issued Nov. 14, 2007 by the USPTO for U.S. Appl. No. 11/051,086.

Office Action issued Jul. 24, 2009 by the USPTO for U.S. Appl. No. 10/934,158.

Office Action issued Feb. 11, 2009 by the USPTO for U.S. Appl. No. 10/934,158.

Office Action issued Jan. 9, 2008 by the USPTO for U.S. Appl. No. 10/934,158.

Office Action issued Jul. 17, 2007 by the USPTO for U.S. Appl. No. 10/934,158.

Office Action issued Jan. 5, 2007 by the USPTO for U.S. Appl. No. 10/934,158.

Office Action issued Sep. 5, 2008 by the USPTO for U.S. Appl. No. 10/934,158.

Office Action issued on Jun. 19, 2009 in related Chinese Application No. 200580036501.4.

* cited by examiner

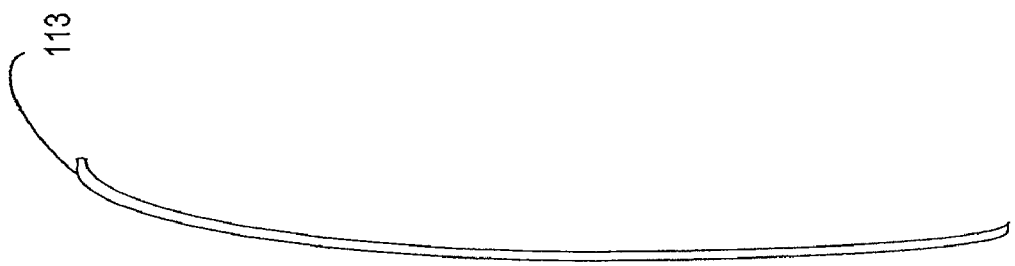

RADIANT THERAPEUTIC HEATING APPARATUS

CROSS REFERENCE TO RELATED APPLICATIONS

This application is a continuation-in-part of U.S. patent application Ser. No. 11/051,086, entitled "Radiant Therapeutic Wrist Heating Pad," to Docherty et al., filed on Feb. 4, 2005, now U.S. Pat. No. 7,693,580, which is in turn a continuation-in-part of U.S. patent application Ser. No. 10/934,158, entitled "Radiant Therapeutic Heater," to Docherty et al., filed Sep. 3, 2004, now U.S. Pat. No. 7,783,361, both of common assignee to the present invention, the contents of which are incorporated herein by reference in their entireties.

BACKGROUND OF THE INVENTION

1. Field of the Invention

This invention relates generally to an improved heating apparatus that has been found to be useful for therapeutic applications, and more particularly to an improved radiant therapeutic heater.

2. Related Art

Certain types of painful conditions of muscles or joints such as, e.g., but not limited to, arthritic pain, often have the application of heat prescribed to relieve the pain. Heat is normally applied in a variety of ways, for instance by the use of irritant rubbing compounds which cause local stimulation of blood vessels thereby increasing body heat carried to the location, the use of infrared lamps, the use of radio frequency apparatus such as diathermy machines, the use of hot water bottles or electrically operated heating pads.

While some or all of the aforenoted apparatuses are alleged to work to some degree, all have certain disadvantages. For instance, the prolonged use of an infrared heating lamp can cause localized burning of the skin. Diathermy machines are specialized apparatuses that require expensive skilled operators. Irritant rubs, while apparently generating local heat, sometimes irritate the skin. Hot water bottles maintain an uneven temperature with time, generally are applied too hot to the skin, and later cool to an ineffective temperature. Thus, hot water bottles are uncomfortable for most of their time of application.

Conventional heating pads generally include insulated electrical heating elements held within a sealed bag, covered with a washable removable cloth envelope. Such heating pads are resistance heated by a flow of electricity therethrough, which heat the surrounding insulated envelope. The conventional pad may be applied to an area of the body which is to be treated, and the hot pad may provide fairly even heat to the skin.

However the use of conventional heating pads must be carefully controlled. Since conventional pads heat the skin by conduction from the heating coils to the body of the user, the pads feel generally hot to the touch, and use must be limited or the skin can be burned, particularly if the user falls asleep on the pad. Due to the conduction of heat to the skin, the pad eventually begins feeling very uncomfortable. While such pads generally utilize thermostats to control the amount of heat generated, the use of conventional pads in a confined space, such as under the patient, generally can cause a build up of heat on the skin which is conducted directly from the heating coils. The heat has been found to eventually become uncomfortable even at a generally low thermostatic setting.

An exemplary, non-limiting, but common, malady for which heat has heretofore not been generally applied is carpal tunnel syndrome, which generally occurs when tendons or ligaments in the wrist become enlarged, often from inflammation after being aggravated. The narrowed tunnel of bone and ligaments in the wrist pinches the median nerve on the palm side of the wrist, nerves that reach the fingers and the muscles at the base of the thumb. This can result in pain, weakness or numbness in the hand and wrist, often radiating up the arm. Carpal tunnel syndrome can be the result of a combination of factors that increase pressure on the median nerve and tendons in the carpal tunnel, rather than a problem with the nerve itself. While the disorder tends to be congenital—the carpal tunnel is smaller in some people than others—other contributing factors include trauma or injury to the wrist that cause swelling. Some cases are due to work-related cumulative trauma of the wrist. Although in some cases no particular cause can be identified, it is generally believed that repetitive and forceful movements of the hand and wrist during work or leisure activities can cause carpal tunnel syndrome.

Carpal tunnel syndrome is generally treated by immobilizing the wrist in a splint to minimize or prevent pressure on the nerves. Medication to reduce inflammation may also be prescribed. In extreme cases, a surgical procedure is performed in which doctors open the wrist and cut the ligament at the bottom of the wrist to relieve the pressure. When using a splint or brace, the user's hand is caused to be placed in a preferred position, with the hand bent at the wrist to relieve pressure on the median nerve. The brace can also provide an additional benefit in that the skin temperature of the user may become slightly elevated and thus provide heat to the user's tendons and ligaments.

What is needed is a brace or splint that can properly position a user's hand with respect to their forearm to alleviate carpal tunnel syndrome symptoms. What is further needed is to provide a carpal tunnel syndrome therapy wrist brace, which brace properly positions the user's wrist while also having a radiant heat therapy unit for decreasing inflammation. Also needed, is to provide a method of treating repetitive strain injuries such as carpal tunnel syndrome. Further needed, is to provide a non-invasive system for the temporary relief of pain associated with repetitive strain injuries.

SUMMARY OF THE INVENTION

An exemplary embodiment of the present invention may be directed to a novel form of an electrically operated heating apparatus. In one exemplary embodiment, the apparatus may be designed specifically for use about a portion of a user (such as a wrist to alleviate symptoms common to carpal tunnel syndrome). The invention, in general, may be a radiant therapeutic heating apparatus comprising a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, and a sealed radiation permeable envelope enclosing the heater. In an exemplary embodiment, the flexible heat generating layer may comprise a foam insulation layer which may be impregnated with a resistive material, which material, may provide a surface temperature, when current is conducted therethrough, which may be in the range of, e.g., but not limited to, about 54 degrees Celsius. The heating apparatus according to another exemplary embodiment of the present invention may also include a stiffener to protect the heating element from damage due to, e.g., but not limited to, bending or creasing of the pad. In one exemplary embodiment, the stiffener may have a slight curve to accommodate the shape of a portion of a user, such as, e.g., but not limited to, so as to position the hand and/or wrist at, e.g., a preferred therapeutic angle.

BRIEF DESCRIPTION OF THE DRAWINGS

A better understanding of the invention and various other features and advantages of the present invention will become readily apparent by reading the following description in conjunction with the drawings, which are shown by way of example only, and not limitation, wherein like reference numeral may refer to substantially alike components:

FIG. 6 is a detailed view of an exemplary stiffening member according to another exemplary embodiment of the present invention.

DETAILED DESCRIPTION OF EXEMPLARY EMBODIMENTS OF THE INVENTION

An improvement over conventional heating pads can be found in U.S. Pat. No. 4,186,294 ("the '294 Patent") which issued on Jan. 29, 1980, of common assignee to the present invention, the contents of which are incorporated herein by reference in its entirety. Briefly, the '294 Patent discloses a therapeutic heating pad which operates using black body radiation of infrared heat, rather than conduction as in conventional pads. The surface temperature of the pad exceeds the temperature of the human body, somewhat, but because of its unique design the heat is dissipated and it does not feel uncomfortably hot to the touch. It can, as a result be used for extended periods of time. Yet the radiant heat generated by the pad has been found to penetrate tissue relatively deeply, thus providing an enhanced therapeutic effect. This is accomplished without the previously encountered hot or burning feeling on the skin of a user.

Figure 1:
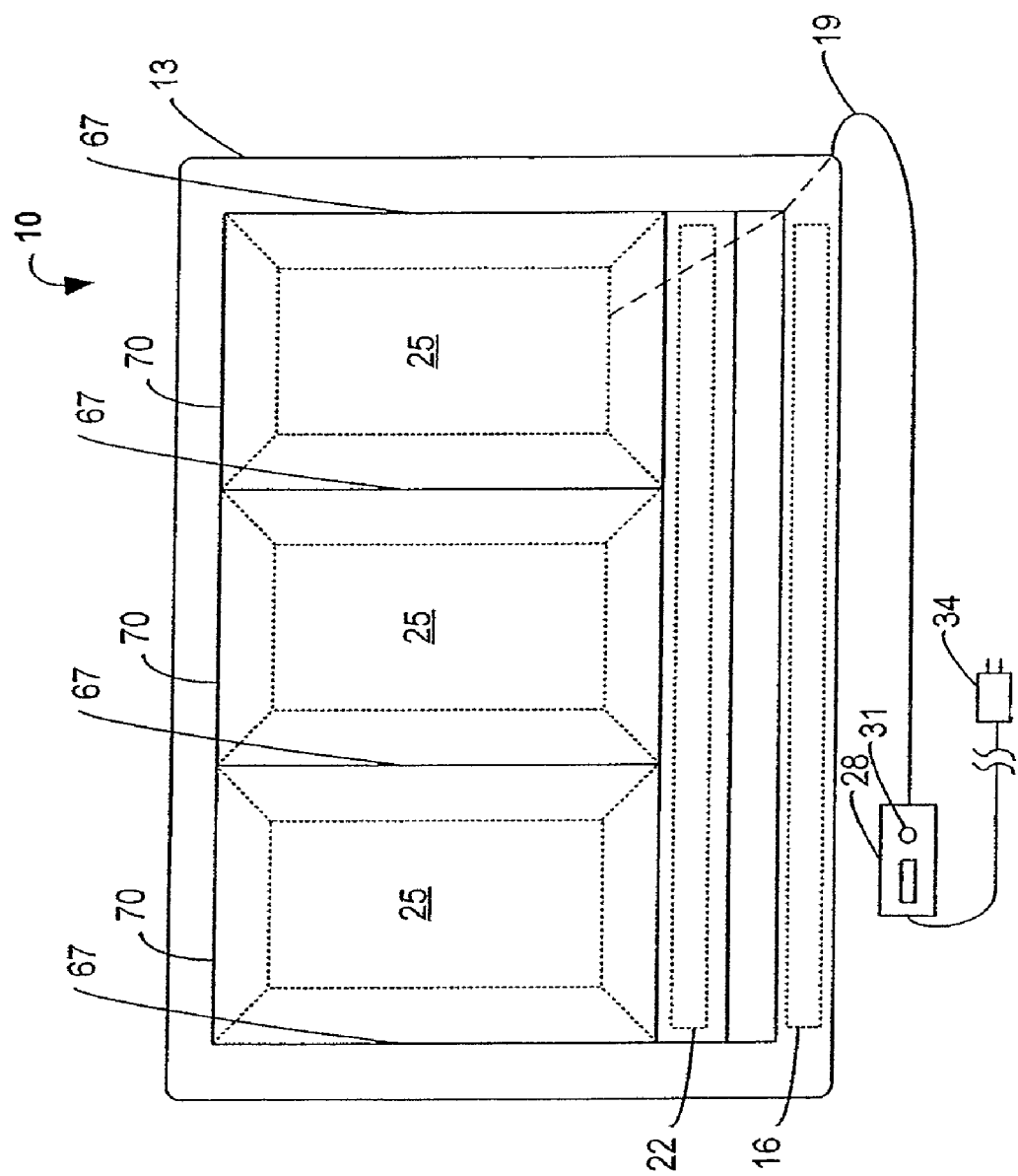
FIG. 1 is an exemplary top perspective view of an exemplary radiant heating apparatus according to an exemplary embodiment of the present invention.

Referring now to the drawings in detail, wherein like reference characters refer to like generally similar elements, there is shown in FIG. 1 an exemplary top perspective view of a radiant heating apparatus 10 according to an embodiment of the present invention and described in applicant's co-pending application U.S. patent application Ser. No. 10/934,158. The heating pad 10, in an exemplary embodiment, may preferably have a cloth cover 13 of cotton, man-made or other natural fiber, formed into an envelope and closed by a fastener 16, such as, e.g., but not limited to, a zipper, preferably a hook and loop fastener 16 such as, e.g., but not limited to, a VELCRO® fastener. In another exemplary embodiment, the cover 13 may be made of any other materials such as, e.g., but not limited to, any textile material, any natural material, any man-made material, polyurethane, nylon, 100% nylon, a nylon-cotton blend, a 50/50 nylon-cotton blend, etc. A power cord 19 may extend from an opening which may be closed by a fastener 22, such as, e.g., but not limited to, a second Velcro zipper fastener 22. The power cord 19 may carry current to one or more heating elements 25 which, in an exemplary embodiment, may be controlled by an inline cord on-off switch 28. The on-off switch 28 may include, in an exemplary embodiment an indicator light 31 as shown.

The on-off switch 28, in another exemplary embodiment may be adapted for remote control. In another exemplary embodiment, the heating device may have a communications device incorporated with it to allow for remote control of the apparatus using, e.g., but not limited to, a remote device, a wireless network, a radio frequency network, an Infrared wireless communications network, a wired network, the Internet. In one exemplary embodiment, the apparatus 10 may be integrated with a microprocessor to allow greater programmability and additional communications capabilities.

The power cord 19 may be coupled to any conventional power source. While a standard 110 volt AC main plug 34 may be shown at the end of power cord 19, it should be noted that upon appropriate design of the heating element 25, other potentials can be used, including, e.g., but not limited to, 12 volts AC or DC, 75 volts AC or DC, 220 volts AC or DC, etc. Also, the source of electrical power may be a battery pack, and/or a re-chargeable battery pack (not shown) for enhanced portability of the heating pad 10.

While the heating apparatus 10 may be referred to as a heating pad 10 in this application, it should be noted that the apparatus need not take the form of a pad. Instead, in other exemplary embodiments, the heating apparatus 10 may include a piece of clothing, a hat, footwear, a blanket, an "electric blanket", a heating blanket, an operative blanket, a bed, a pillow, a kennel liner, a kennel, a horse blanket, an animal blanket, a pet bed, a warming blanket, a blanket for at least one of pre-operative, during operation, and/or post-operative therapy, etc., and/or a combination heating device and additional component, such as, e.g., but not limited to, a wrist support, a joint supporter, a massager, a vibrating device, and/or a whole body vibration (WBV) therapy device, etc. An exemplary embodiment may, e.g., but not limited to, reduce inflammation, pain and/or stress.

In an exemplary embodiment, the surface temperature of the pad apparatus 10 may be no higher than about 54 degrees Celsius and in another exemplary embodiment on the order of approximately (but not limited to) 44-54 degrees Celsius. The desired temperature may vary by the type of user to which the apparatus 10 is to be used. In the case of a human user, the above exemplary embodiments may be most desirable. In other exemplary embodiments such as, e.g., but not limited to, for other mammals, such as, e.g., but not limited to, horses, pets, cats, and/or dogs, other temperatures may be more appropriate. In one exemplary embodiment, the heating apparatus 10 may have a high power setting and/or a low power setting. In an exemplary embodiment, on the low setting, after full heat up, the micron range may hold steady at approximately 9.1376 based on surface temperatures of approximately 44 degrees Celsius. On the high setting, the micron range may be approximately 9.1089 to 8.7778 based on a range of exemplary surface temperatures of approximately 44-54 degrees Celsius. The heating apparatus 10 may come in various power levels including, e.g., but not limited to, 35 watts version may include, e.g., but not limited to, a single 11 inches by 13 inches insert, which may be used, e.g., for treatment of back, hips, and/or shoulders. In another exemplary embodiment, an approximately 8 watts version may include, e.g., but not limited to, one 2 inches by 8 inches infrared inserts for treating, e.g., but not limited to, a wrist, a left hand, a right hand, carpal tunnel syndrome, and/or repetitive stress injury disorders. In another exemplary embodiment, an approximately 36 watts version may include, e.g., but not limited to, three (3) adjustable 3 inches by 8 inches in area, infrared inserts for treating, e.g., but not limited to, almost any area of the user's body. In another exemplary embodiment, an approximately 24 watts version may include, e.g., but not limited to, two 3 inches by 8 inches inserts which may be used for treating, e.g., but not limited to, knee, calf and/or thigh area, tennis elbow, carpal tunnel syndrome, and/or other injuries of the hand, wrist, and/or elbow, a front shoulder area, a rear shoulder area and/or both the front shoulder and rear shoulder areas simultaneously. In yet another exemplary embodiment, an approximately 38 watts version may include, e.g., but not limited to, two 5 inches by 13 inches inserts and third panel of 3 inches by eight inches for treating, e.g., but not limited to, the shoulder area, and/or the collarbone area. In another exemplary embodiment, the heating apparatus 10 may be combined with any of a number of well known therapeutic and exercise related devices, whether electronic, or not. In one exemplary embodiment, the heating apparatus 10 may be combined with, e.g., but not limited to, a massage device, a vibrator, a vibrating device, and/or another other therapeutic device. For further information regarding an exemplary embodiment of a device including a heating pad and massager, see the discussion below with reference to FIG. 4. In another exemplary embodiment, the heating apparatus 10 may be a 95 watts power level apparatus, sufficient for a treatment table's use, of, e.g., but not limited to, approximately 38 inches by 18 inches, which may be sufficient to cover, e.g., a spine area, and/or a full back area including, e.g., but not limited to, from the base of a skull, to tailbone.

Other versions may be available for use with any animals, non-humans, mammals, etc., such as, e.g. but not limited to, a horse, pets, and/or other animals domesticated, or otherwise. According to one exemplary embodiment, an equine therapy version may include, e.g., but not limited to, a model including, e.g., but not limited to two (2) 3 inches by 8 inches pads using 24 watts of power, which may be used, e.g., but not limited to, to treat sinus conditions, for the front sinus, and/or for the throat, etc. In another exemplary embodiment, a model including, e.g.; but not limited to four (4) 3 inches by 8 inches pads using 48 watts of power, which may be used, e.g., but not limited to, to treat temporomandibular dysfunction, giving pain relief and increasing blood flow, using on the temporomandibular joint and/or poll area, etc. In yet another exemplary embodiment, a model including, e.g., but not limited to two (2) 5 inches by 13 inches pads using 26 watts of power, which may be used, e.g., but not limited to, to treat the neck, and throat areas, and/or may be well suited for equestrian competitors. In yet another exemplary embodiment, the heating apparatus to may be a 48 watts power level apparatus, may include, e.g., but not limited to, two (2) approximately 3 inches by 13 inches, models, and two (2) approximately 3 inches by 8 inches, models, or 96 watts for a pair, if used for both front and hind legs of a horse. In another exemplary embodiment, a model including, e.g., but not limited to, a hi-intensity therapeutic blanket, for treatment of, e.g., but not limited to, the central body of an animal using, e.g., but not limited to, twelve (12) pads including pads such as, e.g., but not limited to, six (6) 5 inches by 13 inches pads, which may be used, e.g., but not limited to, to cover the withers, back, loin and croup; and such as, e.g., but not limited to, six (6) 11 inches by 13 inches pads, which may be used, e.g., but not limited to, to cover the shoulder, barrel, thigh, and lung areas, and may be used to service bleeders, and may use, e.g., but not limited to, approximately 288 watts of power. The equine therapy systems may be used for, e.g., but not limited to, relief of pain and/or soreness in muscles and/or joints, may remove lactic acid build-up in muscles, may remove soreness due to injury, may remove inflammation of joints caused by arthritis, may remove sinus inflammation, and/or pre-competition to improve performance levels, may enhance respiratory system, may remove sinus congestion, may act as a diuretic and may help bleeders, may reduce lactic acid levels to prevent tying up during competition, helping a non-sweater sweat, increasing kidney function, help bring out natural oil of the skin, helping make hair glisten, treats colic.

As is common with conventional heating pads, the on-off switch 28 may incorporate a variable temperature control. In one exemplary embodiment, the heating apparatus 10 may include a rheostat to, e.g., but not limited to, control electrical flow for an operative blanket application. Even at the 54 degrees Celsius temperature the heating pad apparatus 10 may be safer for application to the skin of the user, while it has been found that the infrared radiation provided by the device of the present invention still may penetrate deeply into the body and muscle of the user for the desired therapeutic benefit of the heating pad. Consequently the heating pad 10 can be used in place for even more extended periods of time than conventional heating pads, with a comfortably warm feeling, and without causing surface skin burns. In an exemplary embodiment of the heating apparatus 10 including the rheostat for use, e.g., but not limited to, as an operative blanket, a minimum temperature of approximately 38 degrees Celsius may be achieved, i.e., approximately 6 degrees lower than some of the other exemplary embodiments.

Figure 2:
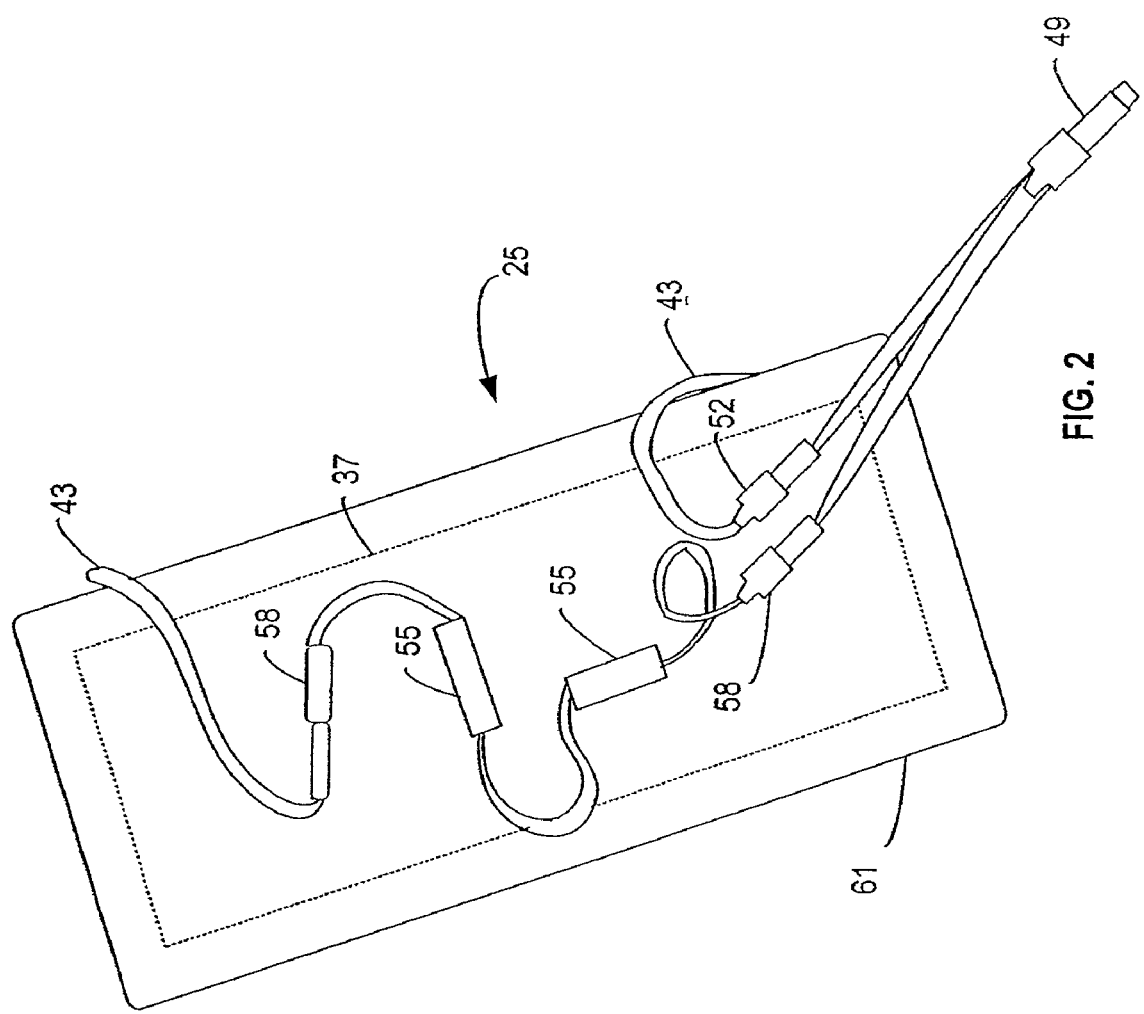
FIG. 2 is an exemplary detailed view of an exemplary radiant heating element for the heating apparatus according to an exemplary embodiment of the present invention.
Figure 3:
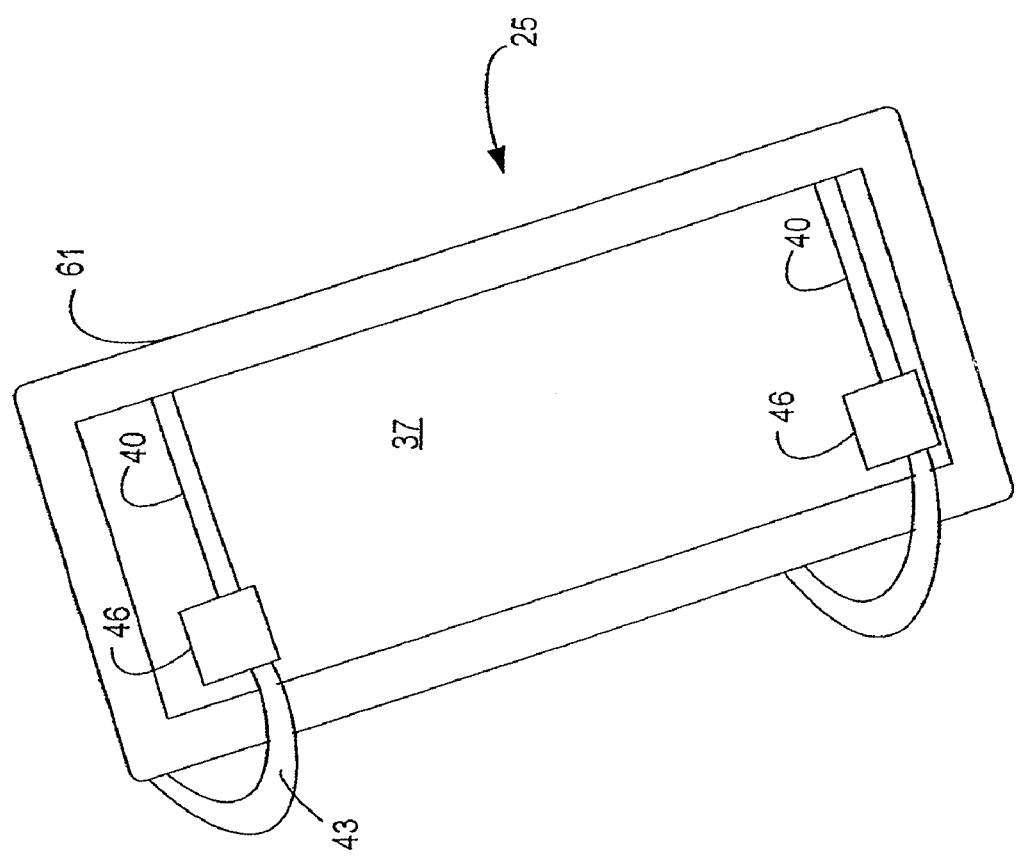
FIG. 3 is an exemplary plan view of the reverse side of FIG. 2 of the exemplary radiant heating element showing the heat generating layer.

FIGS. 2 and 3 show an exemplary embodiment of a heating element 25, which may be used within the heating pad apparatus 10 according to the exemplary embodiment of the present invention. The heating element 25 may include a fiberglass mat or layer 37. The fiberglass layer 37 may be, in an exemplary embodiment, preferably thoroughly, impregnated and saturated with a chemical compound, which may in an exemplary embodiment be a mixture of low and high resistance carbon to provide a desired, or required, resistance, in an exemplary embodiment. In one exemplary embodiment, saturation may be carried out in such manner as to insure that fiberglass may be throughly covered inside and out homogeneously. Following saturation, the material may be passed through a series of steel rollers which may remove excess wet chemical, after which, in an exemplary embodiment, the material may be passed through an oven drying process and may be finally subjected to heat of, e.g., but not limited to, about 425 degrees Celsius to, e.g., extract any remaining moisture in the material, thus stabilizing the carbon-graphite impregnated material. According to an exemplary embodiment of the present invention, the coating materials of the kind preferred to be used in the heating element of this invention are described in U.S. Pat. No. 3,865,626, issued Feb. 11, 1975, the contents of which are incorporated herein by reference in their entirety.

The quantity of the material impregnated in the fiberglass, which may form a resistive layer, may range from about 0.1 grams per square meter to about 3 grams per square meter. According to an exemplary embodiment of the present invention, after heat treatment, drawing and passing of the fiberglass through the rollers (the latter of which may gauge the thickness of the particles of the impregnate adhering to the material) may set the resistivity of the material.

It should be noted that materials other than fiberglass could alternatively be used as a base for the resistive material according to another exemplary embodiment. For instance, as described in U.S. Pat. No. 3,865,626, a polyester film may be treated with a solvent or swelling agent. Electroconductive particles, preferably carbon black may be applied to the treated surface in a concentration corresponding to the desired resistance. The film may then be subjected to heat treatment to solidify and retain the resistive material in the surface. It should be noted that since the resistance material is basically fabricated of carbon compound, the heating element 25 may be a black body radiator, which may have a high efficiency of radiant heat dispersion which, it is believed, may contribute to the effectiveness of the invention.

Referring to FIG. 3, conductive tapes 40, preferably of copper foil, may be sewn into electrical contact with the resistive material along parallel edges of the fiberglass layer 37. The tapes 40 can be made of either woven or non-woven material. A pair of wires 43 may then be electrically connected to the tapes 40 via a fastener 46, such as, e.g., but not limited to, by a clip 46. In an exemplary embodiment of the present invention, clip 46 may be an alligator clip, or the like. The other ends of the electrical wires 43 may be operatively connected (or coupled) to a quick connector 49, as shown in FIG. 2, which may be connected to a complementary connector (not shown) to individually connect (couple) each heating element 25 to the main power cord 19.

According to an exemplary embodiment, an alligator assembly may be used. According to an exemplary embodiment, the full assembly may include, e.g., but not limited to, a 4 inch insulated 18 gauge wire, with (in an exemplary embodiment) a male metal end on one end of the wire, and an alligator clip on the other end. The alligator assembly may be secured to foil just below the edge of the element. The heating element with alligator assembly attached may be laminated, according to an exemplary embodiment. According to an exemplary embodiment, any laminate, including any excess laminate around the element, may be trimmed. According to an exemplary embodiment, any corners may be rounded and/or softened. According to an exemplary embodiment, the laminate may be, e.g., but not limited to, a 10 mil laminate such as, e.g., but not limited to, a MYLAR® laminate. After lamination, according to an exemplary embodiment, a single male plastic cap may be placed on the ends of each alligator wire.

It should be noted that as the resistivity of the material 37 may be measurable in ohms per square units, the material could be made in large sheets or rolls, and may be cut to a desired (or required) resistance. In a preferred exemplary embodiment, the heat element may dissipate 26.3 watts per square foot with an input voltage of, e.g., but not limited to, 110 volts AC, and/or 220 volts, 240 volts, etc. Depending on the specific design, however, the dissipation can be made as low as thirteen (13) watts per square foot. The individual heating elements 25, and thus the overall heating pad 10, can be made a variety of desired dimensions in length or width depending on how and where the heating pad may be used on a particular body part of the user. For example, "dedicated" heating pads can be designed for use on, e.g., but not limited to, a user's wrist, shoulders, knees or thighs and can be made so as to have securing straps for holding the heating pad in place for the best therapeutic effect. Moreover, although three (3) heating elements 25 are shown in the exemplary embodiment of FIG. 1, a larger, single heating element can be used, as well as one or more smaller units. According to another exemplary embodiment, a professional unit may include large version, which may be used for a treatment table, which may use, e.g., but not limited to, six (6) or more heating elements. According to an exemplary embodiment, an operative blanket may be provided. In one exemplary embodiment, the operative blanket may be used, e.g., but not limited to, prior/during, or after an operation. In an exemplary embodiment, the operative blanket may have a minimum operating temperature of, e.g., but not limited to, 38 degrees Celsius. In an exemplary embodiment, the operative blanket may include, e.g., but not limited to, a control switch such as, e.g., but not limited to, a high/low switch, a rheostat, and/or variable resistor dial, which may be adapted to control power. According to another exemplary embodiment, particular models may include, in addition to one or more heating elements, another electronic device such as, e.g., but not limited to, a massage and/or vibration device (as discussed in FIG. 4 below) and/or another therapy device. In one exemplary embodiment, an equine heating blanket apparatus 10, may include, e.g., but not limited to, as many as, six, twelve (12), or more, heating elements.

As shown in FIG. 2, each wire 43 may be individually (or jointly) connected to (or coupled to) the quick connector 49 and one of the conductive tapes 40 (see FIG. 3) in order to complete the electrical circuit. One of the wires may be connected to, or coupled to, the quick connector 49 via a second quick connector 52. The other wire may be connected to, or coupled to a second quick connector 58 via, e.g., one or more current limiting thermostats 55. In one exemplary embodiment, the heating apparatus 10 may include a thermostat 55. In another exemplary embodiment, the heating apparatus 10 may include at least two thermostats 55, as shown in the exemplary embodiment of FIG. 2, where the second thermostat may serve as a safety backup in the event of failure of the first thermostat 55. In the preferred exemplary embodiment, two (2) thermostats 55 may be used, one acting as a back-up in the event of failure of the other. According to the exemplary embodiment, the thermostats 55 may be coupled or connected in series with the heating element 25. The thermostats 55 may cut off power to the heating element 25 in the event that the temperature becomes excessive. According to one exemplary embodiment, one or more of thermostats 55 may be self resetting thermostats capable of being reset by removing power from the thermostats, and by having the temperature sensed fall below a given threshold. The thermostats 55 may preferably be connected to, or coupled to, the wire 43 and quick connector 49 via, e.g., but not limited to, a pair of in-line quick connectors 58 for ease of replacement, in one exemplary embodiment. Thus at least one current limiting control thermostat 55 may be within the electrical circuit of the heating element 25 and may be distributed to sense whether any hot spots may be developing due to a fold, or the like in the heating pad 10. According to an exemplary embodiment, the thermostat may be a thermostat sensor, and may include, e.g., but not limited to, a single plastic female cap, in an exemplary embodiment, as an exemplary quick connector.

In order to prevent the wires 43 and/or the thermostats 55 from being inadvertently creased or bent, which may cause a power surge within the heating element 25, in one exemplary embodiment, these components may be attached to a stiffening member 61. Preferably, the stiffening member 61 may be a relatively thin layer of propylene material of about three-sixteenths (3/16) of an inch thick. According to one exemplary embodiment, the stiffener may be made of polypropylene. According to an exemplary embodiment, the stiffening member 61 may be cut to a desired dimension, and then the corners may be rounded using, e.g., but not limited to, a router, to an approximately 0.25 inch radius arc. According to an exemplary embodiment, the stiffener 61 may be coupled, or attached to the element using, e.g., but not limited to, a fastener, adhesive, and/or tape. According to an exemplary embodiment, tape may be MYLAR® tape. According to an exemplary embodiment, the foil side of the heating element may face the stiffener 61.

According to an exemplary embodiment, the thermostat 55 may be taped onto the element assembly with the metal side of the thermostat against the element.

In an exemplary embodiment, there may be disposed against the surface of the stiffening member 61, which may also be against the thermostats 55, an insulating layer (not shown), which may more fully protect the individual components of the heating element 25. In an exemplary embodiment, the insulating layer may be made of a foam insulation of, e.g., but not limited to, between about one-quarter (¼) and one (1) inch in thickness, and/or may be 1 inch thick in another exemplary embodiment.

Additionally, in an exemplary embodiment, each of the heating elements 25 may be preferably encased within an envelope (not shown) so that only the quick connector 49 may protrude therefrom. In an exemplary embodiment, the envelope may be, e.g., but not limited to, polyvinylchloride (PVC) (or vinyl). In an exemplary embodiment, the heating element 25, foam and a PVC layer with the shiny side facing inside may be sandwiched together and laminated and the excess may be trimmed. In the event that a new heating element may be required, in an exemplary embodiment, the cover 13 may be opened and the quick connector may be disconnected. A new heating element 25 may then be connected (or coupled), the element 25 may be inserted into the cover 13, and the Velcro zippers 16, 22 may be resealed. This envelope may hold, in an exemplary embodiment, all of the above-described elements in a laminated position, and may protect the elements against intrusion of moisture or other contaminants. The pair of wires 43, in an exemplary embodiment, which may contact the conductive tapes 40 via, e.g., but not limited to, the clips 46, may extend through a hole (not shown) in the vinyl envelope, which hole may be preferably sealed against the wires 43. Alternatively, in an exemplary embodiment, the quick connector 49 itself can be a sealed connector (or coupler) projecting from the vinyl envelope, if desired. Referring to FIG. 1, in an exemplary embodiment, the area between the zippers 16, 22 may hold the various wires and connectors for the heating elements 25.

As shown in FIG. 1, the outer cloth cover (or bag) 13 may enclose each vinyl envelope and hence each heating element 25. Preferably the cloth cover 13 may, in an exemplary embodiment, be fabricated of terry towel, which has been found to be most comfortable to the user, or other cotton, man-made or natural fiber material. As noted above, the cloth cover 13 can be closed by one or more fastening devices, such as, e.g., but not limited to, a zipper, and/or a hook and loop closure zipper (generally referred to as a VELCRO® fastener), or the like. The cover 13 may thus be removed and washed as desired. In a preferred exemplary embodiment, the cover 13 may have two halves, and each half of the cover 13 may be stitched together with stitches 67 as shown in FIG. 1, so as to create one or more individual pockets 70 into which each heating element 25 may be inserted. In an exemplary embodiment, the segmenting of the heating apparatus 10 with stitched pockets 70 may also allow the heating pad 10 to be bent along the area of the stitching 67 to conform to a body part of the user, while each heating element 25 may be prevented from being creased by the stiffener 61. The thermostats 55, in an exemplary embodiment, may further prevent temperature spikes in the event that any of the electrical wires or cords are creased or bent.

In operation, the heating pad 10 may be plugged in or otherwise connected to a source of electrical current. The power source, in an exemplary embodiment, may be integrated into the heating pad 10, and may include, e.g., but not limited to, a battery supply, a rechargeable battery, a solar panel, alternative energy source, or the like. The heating pad 10 may be placed over a region to be therapeutically warmed with deep heat. Current may pass through the resistance material of the fiberglass layer 37, in an exemplary embodiment, which may create a source of black body infrared radiation. The radiation may be received by the body of the user, and penetrates deeply beneath the skin to the users underlying muscle. In an exemplary embodiment, although the heat may penetrate deeply, the heating pad 10 does not feel uncomfortably hot to the touch, as it does not exceed, approximately 54 degrees Celsius (about 129 degrees Fahrenheit), and may be about 44-54 degrees Celsius (111-129 degrees Fahrenheit). According to another exemplary embodiment, the surface temperature may be, e.g., but not limited to, 49-54 degrees Celsius (120-129 degrees Fahrenheit).

Figure 4:
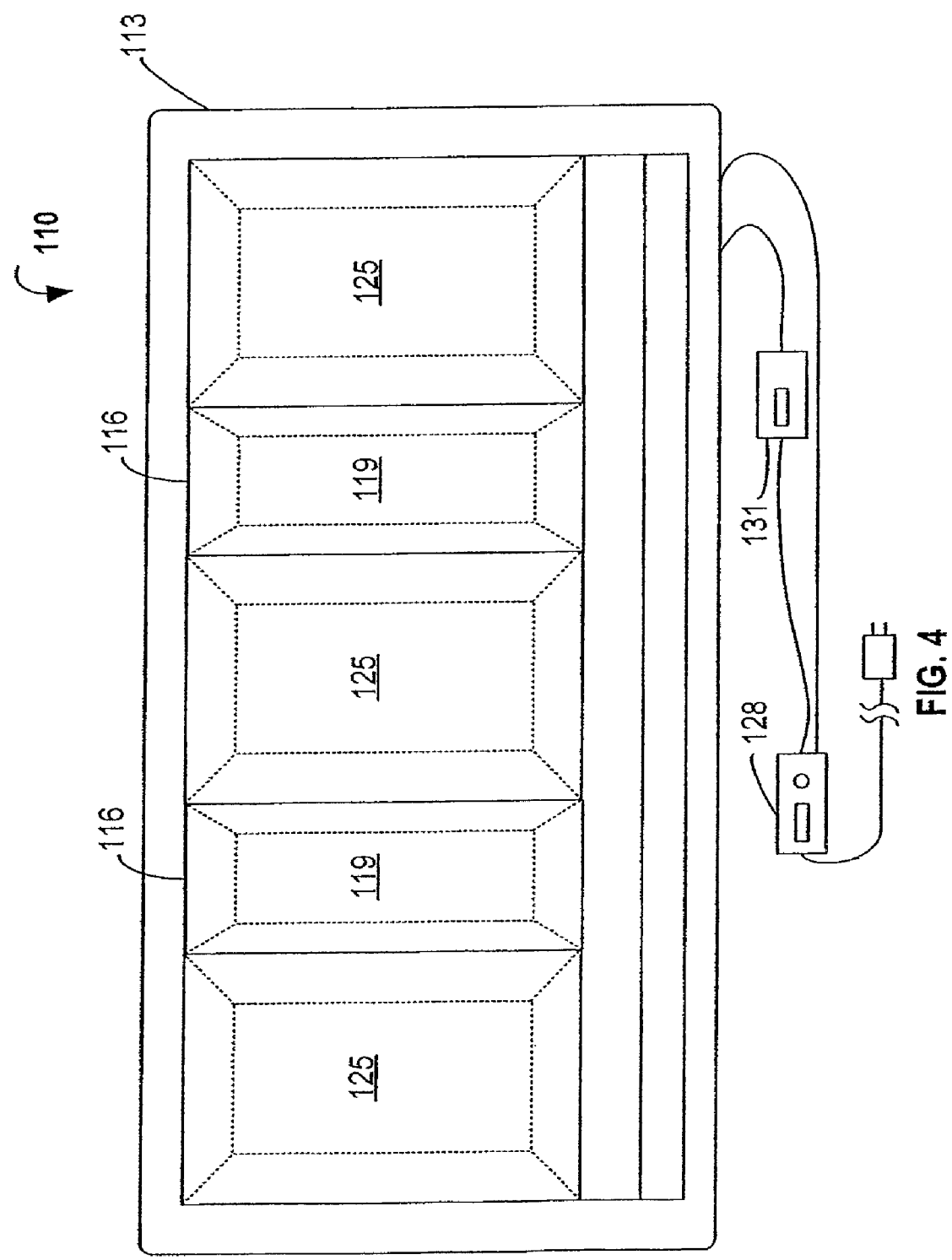
FIG. 4 is an exemplary top perspective view of a second exemplary embodiment of a radiant heating apparatus according to another exemplary embodiment of the present invention.

FIG. 4 shows an alternate exemplary embodiment of a vibrating heating pad apparatus 110. In this exemplary embodiment, the cover 113 may include one or more pockets 116 which may house vibrating elements 119 for providing this added therapeutic benefit to the user. Similar to that of the heating elements 125, each vibrating element 119 may be connected (or coupled) to a switch 128 which may preferably have a separate control 131 for the heating elements 125 and vibrating elements 119. As with the heating pad 10, the control 131 for the vibrating elements 119 may include variable speeds.

In the event that the heating pad 110 may be heated before being applied to the user's body, should the heating pad have a resistivity, which may raise its temperature higher than that of the temperature of the human body, the pad may feel warm for an instant when first applied to the body of the user. However it has been found that this warmth may be almost instantly dissipated by the skin of the user, and further contact with the pad does not impart an uncomfortably hot sensation to the touch. Accordingly there may be very little heat conduction from the inventive structure, but there is substantial radiated heat. The pad may include foam. The radiated heat may be received by receptive bodies opposite the emitting side of the heating pad 10. Yet the air that may be in contact with the heating pad does not heat, since it may be transparent to infrared radiated heat.

It has been found that the described structure radiates heat in a wavelength band of, e.g., but not limited to, between approximately 5 and 25 microns, 9.1-11 microns, 9-11 microns, 9.1-12 microns, and/or 9-12 microns, while 9-12 microns may be optimum, etc., while the entire infrared bandwidth may extend between approximately 0.72 and 3100 microns. It is believed, that the particular bandwidth of the radiation which is emitted by this invention contributes to the apparent deep penetration and therapeutic effect obtained.

As noted earlier, the radiant heating pad or apparatus can be made of various sizes, such as, e.g., but not limited to, the sizes given by the exemplary embodiments suggested herein, blanket size, or, e.g., of particular shape to match a shape of a portion of a user's body. In one exemplary embodiment, the heating apparatus may be formed to match a user's wrist for use in providing therapy for carpal tunnel and other repetitive stress injuries. In other exemplary embodiments, the heating apparatus may be used for other therapies such as, e.g., but not limited to, head, neck, temporomandibular joint, poll, face, shoulders, collarbone, leg, heel, foot, knee, bicep, tricep, calf, quadracep, plantar fascia, hamstring, hip, ankle, hand, arm, forearm, elbow, abdomen, back, spine, upper and/or lower back, gluteals, other muscles, joints, and/or extremities, etc.

Wrist Therapy Heating Apparatus Exemplary Embodiment

Figure 5:
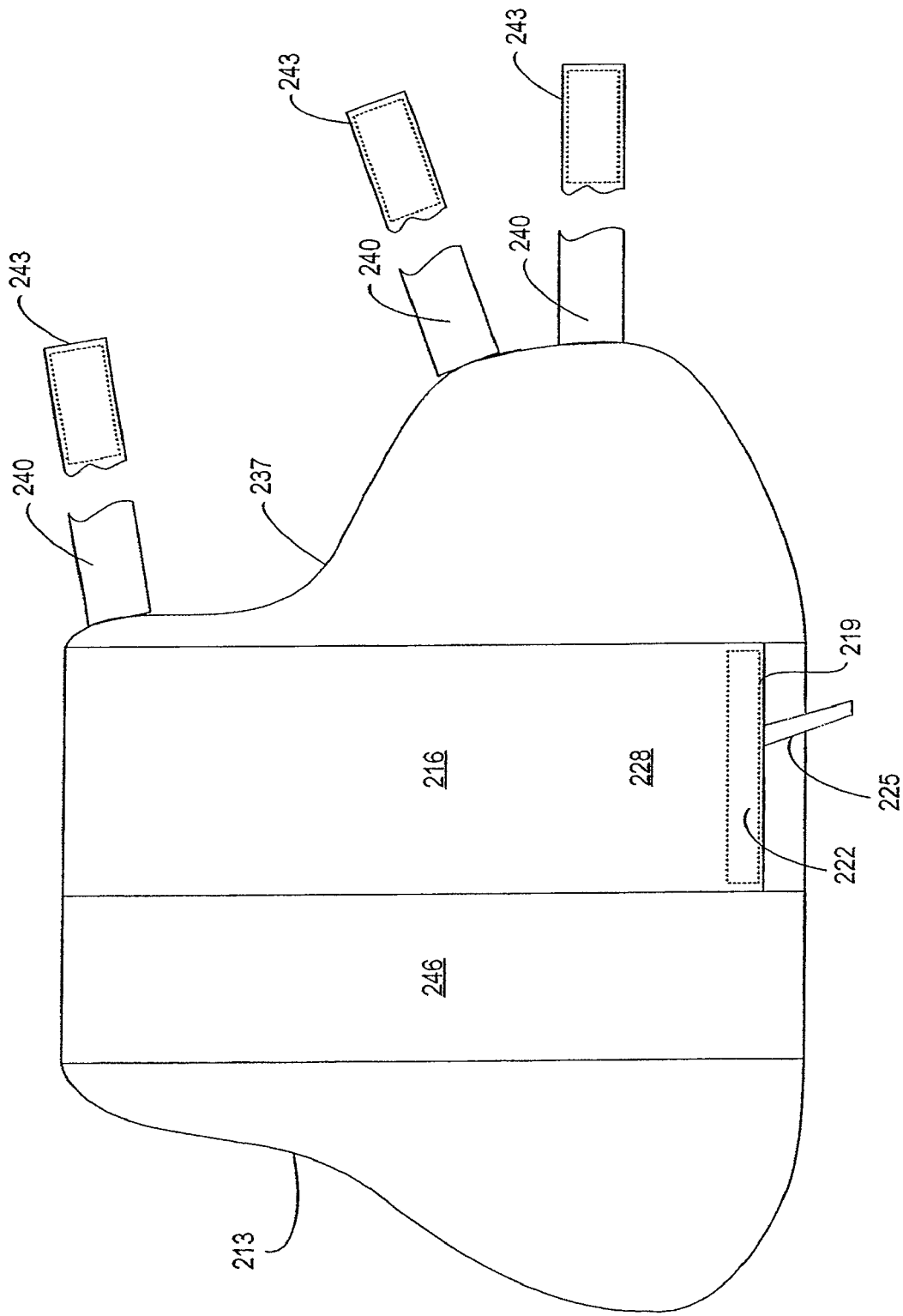
FIG. 5 is an exemplary top view of an extremity (such as wrist) radiant heating apparatus according to another exemplary embodiment of the present invention.

FIG. 5 depicts an exemplary embodiment of a heating apparatus shaped to a portion of a user's body, in this case, e.g., but not limited to, a wrist radiant heating pad according to the present invention designed to alleviate symptoms commonly associated with repetitive strain injuries (RSI).

The wrist radiant heating pad 210, according to an exemplary embodiment, may include a cloth cover 213 of cotton, man-made or other natural fibers, and may have formed therein a pocket 216 which may have an opening 219, which preferably may be closed by a fastener 222, such as, e.g., but not limited to, a zipper, and/or a Velcro zipper 222. A power cord 225 may extend from the opening 219 and may be operatively connected (or coupled) between a radiant heating element 228 which may be enclosed within the pocket 216, and a source of electric power. The heating pad 210 may be preferably controlled by an in-line cord and a power control switch such as, e.g, but not limited to, a rheostat, a toggle switch, an on-off switch, a high-low, a multi-level switch, a dial, digital, analog, and/or other control switch, which may have an indicator light as shown in FIG. 4, similar to that shown in FIG. 1. The connection to a power source may be through an electrical outlet plug (not shown), to a battery pack (not shown), and/or other energy source.

The design, according to an exemplary embodiment, of the wrist radiant heating pad 210 may allow the pad apparatus 210 to be wrapped about a user's wrist on either the right and/or left arm, with the user's thumb being positioned adjacent the angled portion 237. The pad may be then wrapped about the user's arm adjacent the wrist, and secured in place by one or more, according to an exemplary embodiment, preferably three, flexible straps 240. The end 243 of each strap 240 may be secured to an opposite portion 246 of the pad 210 by a fastener, such as, e.g., but not limited to, Velcro fasteners. Preferably, according to an exemplary embodiment, the strap end(s) 243 may include the hook portion while the opposite portions 246 may include the loop portion of the Velcro so as to snugly and properly fit the heating pad 210 to the user's wrist, such that the heating element 228 may be positioned so as to provide the optimum therapeutic benefit to the user.

As described in Applicant's co-pending application, the heating element 228 may include, according to an exemplary embodiment, a fiberglass mat or layer 249 having the desired resistive properties generally shown in FIGS. 2 and 3. However, for the present invention the stiffening member 252 may be curved, according to an exemplary embodiment, so as to put the user's wrist in the proper position to alleviate the pinch on the median nerve, and thus may provide the preferred therapeutic benefit to the user. As shown in more detail in FIG. 6, according to an exemplary embodiment, the stiffening member 252 may be preferably curved at an angle of about ±5 degrees, and, in one exemplary embodiment, the concave side may be adjacent the user's forearm. Although the heating element 228 may be of any dimension, the heating element 228, according to an exemplary embodiment, may be approximately 2 inches by 8 inches, such that the heating pad 210 may fit comfortably on the user's inside forearm and wrist.

In order to treat symptoms typically associated with repetitive strain injuries such as, e.g., but not limited to, carpal tunnel syndrome, the following method may be used. The heating pad 210 of the present invention may be fitted against the user's inside forearm and wrist and the straps 240 may be adjusted for a comfortable fit, according to an exemplary embodiment. The curve of the stiffening member 252, in an exemplary embodiment, may help orient the affected area in a predetermined therapeutic position. Electrical power may be provided to the device and the radiant heating element 228 may be energized. The heating pad 210 may be applied to the affected area for a predetermined amount of time, such as, e.g., but not limited to, about 30-45 minutes as may, e.g., but not limited to, be prescribed by the user's doctor and/or physical therapist, etc. Because of the design of the present invention, the heating apparatus 210 may be used, e.g., but not limited to, in the home, and/or the user's workplace, while the user may be engaging in his or her normal activities. Preferably, in an exemplary embodiment, the user may treat the affected area for at least two (2) treatment sessions per day, again as prescribed by a doctor or therapist. The radiant heating caused by use of the radiant heat apparatus 10, 210 on the user's forearm and wrist, may increase blood flow to the nerves that control pain and hand sensation to relieve pain and/or numbness. In this manner, the radiant therapeutic wrist heating pad 210 of the present invention may reduce the inflammation and may alleviate the pain of repetitive strain injuries (RSI), and/or carpal tunnel syndrome, etc.

Accordingly a heating pad apparatus 10, 210 has been invented which has significant advantages over conventional therapeutic heat applying devices. Since the pad 10, 210 may give its deep heat penetration by radiation, with what may be a relatively low surface temperature, skin surface burns do not result from prolonged use. The pad may be useable by the patient, and no specialist may be required for its application. In an exemplary embodiment, nonconductive and virtually entire radiative infrared heat in the range of, e.g., but not limited to 5-25 microns, 9 to 11 microns, 9.1-12 microns, 9.1-11 microns, and/or 9-12 microns, may be imparted to the user, according to an exemplary embodiment, which has been found to result in a penetrating deep heat, which patients have found may be highly successful in relief of symptoms of such ailments as, e.g., but not limited to, arthritic pain, etc. According to an exemplary embodiment, 9-12 microns may provide optimum performance.

It may now become evident to a person skilled in the art, understanding this invention, and the exemplary embodiments outlined, that other materials than the ones described can be substituted for the ones described, and that other embodiments and configurations may now be designed. All are considered within the scope and sphere of the invention, as defined in the appended claims. For example, while the invention has been described as having a single radiant heating element, two or more smaller elements may be used for more localized heating. While specific exemplary embodiments of the invention have been shown in the drawings and described in detail, it will be appreciated by those skilled in the art that various modifications and alternatives may be developed in light of the overall teachings of the disclosure. Such changes and modifications may be made without departing from the spirit and scope of the present invention and without diminishing its attendant advantages. Accordingly, the particular arrangements disclosed herein are meant to be illustrative only and not limiting as to the scope of the invention, which is to be given the full breadth of the appended claims and in any and all equivalents thereof.

What is claimed is:

1. A radiant therapeutic heating apparatus comprising:
   at least one radiant heating element electrically coupled to a source of electrical energy adapted to radiate energy at a wavelength which penetrates into a body; a stiffening member adapted to prevent creasing of said radiant heating element; a control switch adapted to vary the level of radiant energy, said control switch comprising at least one of a high/low switch or a multiple level switch; and a cover having a pocket for housing said at least one radiant heating element, wherein the apparatus is adapted to conform to a portion of a user's body in a therapeutic position.

2. A method of using the apparatus of claim 1 for treating repetitive strain injuries of a user, said method comprising the steps of: (a) providing a radiant heating apparatus; (b) fitting the radiant heating apparatus about an affected area of the user; (c) energizing the radiant heating apparatus for a predetermined period of time; (d) de-energizing the radiant heating apparatus; and (e) repeating the step of energizing the radiant heating apparatus.

3. The method of treating repetitive strain injuries of a user of claim 2, wherein the predetermined time period is about 30-45 minutes.

4. The method of treating repetitive strain injuries of a user as recited in claim 2, further comprising the step of orienting the affected area of the user in a therapeutic position.

5. The method of treating repetitive strain injuries of a user as recited in claim 4, wherein the predetermined time period is about 30-45 minutes.

6. A radiant therapeutic heating apparatus of claim 1, further comprising a thermal insulation layer disposed adjacent to said stiffening member.

7. A radiant therapeutic heating apparatus according to claim 6, wherein said thermal insulation layer comprises foam insulation.

8. A radiant therapeutic heating apparatus according to claim 6, wherein said thermal insulation layer comprises a foam insulation of approximately 1 inch in thickness.

9. A radiant therapeutic heating apparatus according to claim 6, comprising a sealed radiant energy permeable envelope adapted to enclose said at least one radiant heating element and said stiffening member.

10. A radiant therapeutic heating apparatus according to claim 9, comprising a plurality of heating elements and wherein the cover comprises one or more individual pockets into which each of said at least one heating elements is inserted.

11. A radiant therapeutic heating apparatus according to claim 9, wherein the cover comprises two halves, and each half of the cover is segmented so as to create one or more individual pockets into which each heating element is inserted.

12. A radiant therapeutic heating apparatus according to claim 9, wherein the cover comprises two halves, and each half of the cover is stitched together with stitches so as to create one or more individual pockets into which each heating element is inserted.

13. A radiant therapeutic heating apparatus according to claim 9, wherein the cover comprises at least one of a cloth cover, a cotton cover, a man-made fiber cover, or a natural fiber cover; and wherein said cover comprises a fastener comprising at least one of a fastening means, an adhesive, a magnet, a zipper, Velcro, a loop and hook fastener, a button, or a snap.

14. A radiant therapeutic heating apparatus according to claim 9, further comprising an enclosure adapted to at least one of enclose or integrate with said sealed radiant energy permeable envelope, said enclosure comprising at least one of: a pad; a blanket; a treatment blanket; an operative blanket adapted for use at least one of before, during or after an operation; a pillow; a bed; an animal blanket; an equine blanket; a kennel liner; a kennel; clothing; footwear; a hat; a pet bed; a warming blanket; a therapeutic support; a massaging device; a vibration device or a pad adapted to heat a portion of a body comprising at least one of a heel, ankle, planter fascia, hamstring, knee, calf, thigh, elbow, collarbone, shoulder, head, neck, temporomandibular joint, poll, wrist, back, hip, leg, foot, wither, back, spine loin, barrel, lung, sinus, respiratory system, kidney, abdomen, a muscle, limb, or joint.

15. A radiant therapeutic heating apparatus according to claim 1, wherein a user of the apparatus comprises at least one of: a mammal; a living being; a human; an animal; a pet; a horse; a cow; a dog; a single hump camel; a two hump camel; or a cat.

16. A radiant therapeutic heating apparatus according to claim 1, wherein the portion of the user's body comprises at least one of: a heel, a hamstring, an ankle, a planter fascia, a foot, a knee, a calf, a thigh, an elbow, a collarbone, temporomandibular joint, poll, a head, a neck, a shoulder, a wrist, a back, a spine, an abdomen, a hip, a leg, a wither, a loin, a barrel, a lung, a sinus, a respiratory system, a kidney, a muscle, a limb, or a joint.

17. A radiant therapeutic heating apparatus according to claim 1, wherein said stiffening member is shaped so as to position the portion of the user's body in a therapeutic position.

18. A radiant therapeutic heating apparatus according to claim 17, wherein the stiffening member is curved.

19. A radiant therapeutic heating apparatus according to claim 1, wherein said radiant heating element comprises a fiberglass material impregnated with resistive material.

20. A radiant therapeutic heating apparatus according to claim 19, wherein the resistive material provides radiant energy at wavelengths between 5 and 25 microns.

21. A radiant therapeutic heating apparatus according to claim 1, further comprising resistive material adapted to provide radiant energy at wavelengths between 5 and 25 microns.

22. A radiant therapeutic heating apparatus according to claim 1, wherein a resistivity of said radiant heating element provides a surface temperature adjacent the body to be heated which is less than or equal to about 54 degrees Celsius.

23. A radiant therapeutic heating apparatus according to claim 1, wherein said stiffening member is a resilient stiffener comprises a warp-resistant material.

24. A radiant therapeutic heating apparatus according to claim 23, wherein said resilient stiffener comprises polypropylene.

25. A radiant therapeutic heating apparatus according to claim 1, further comprising a first current limiting thermostat.

26. A radiant therapeutic heating apparatus according to claim 25, wherein said radiant heating element further comprises a second current limiting thermostat as a safety backup to said first current limiting thermostat.

27. A radiant therapeutic heating apparatus according to claim 1, wherein said heating element comprises a resistive material and at least two current limiting thermostats electrically coupled between the source of electrical energy and the resistive material such that said radiant heating element is adapted to provide radiant energy at wavelengths between 5 and 25 microns wherein a surface temperature is less than or equal to 54 degrees Celsius.

28. A radiant therapeutic heating apparatus according to claim 1, wherein each of said radiant heating elements further comprises: a first current limiting thermostat electrically coupled to said wire adapted to apply electrical current to said conductive tapes; and a second current limiting thermostat electrically coupled to said wire, wherein said first and said second current limiting thermostats act as redundant backups to one another, ensuring cut-off of said radiant heating element in the event of excessive heat and malfunction of either of said first and second thermostats.

29. A radiant therapeutic heating apparatus comprising: a plurality of radiant heating elements electrically coupled to a source of electrical energy adapted to radiate energy at a wavelength which penetrates into a body; a stiffening member adapted to prevent creasing of said radiant heating elements; and a cover segmented into two or more individual pockets each containing at least one of the plurality of heating elements thus allowing the heating apparatus to be bent along the segmented area to conform to a portion of a user's body in a therapeutic position, wherein the heating apparatus is segmented with stitched pockets allowing the heating apparatus to be bent along the area of the stitching to conform to a body part of a user.

30. A radiant therapeutic heating apparatus according to claim 1, further comprising: a power source adapted to provide power to said radiant heating element comprising at least one of a battery, a rechargeable battery, an electrical outlet, a solar cell, or an alternative energy source.

31. A radiant therapeutic heating apparatus according to claim 1, wherein the apparatus comprises a pad; a blanket; a treatment blanket; an operative blanket adapted for use at least one of before, during or after an operation; a pillow; abed; an animal blanket; an equine blanket; a kennel liner; a kennel; clothing; footwear; a hat; a pet bed; or a warming blanket.

32. A radiant therapeutic heating apparatus according to claim 1, further comprising a vibrating device.

33. A radiant therapeutic heating apparatus according to claim 32, wherein said vibrating device includes an electrical switch for separately activating said vibrating device.

34. A radiant therapeutic heating apparatus according to claim 1 further comprising: a vibrator; a power cord adapted to supply electrical energy to said radiant heating element and said vibrator from the source of electrical energy; a first switch for activating said radiant heating element such that a surface temperature of the heating apparatus is about equal to or less than 54 degrees Celsius; a second switch for activating said vibrator; and a bag for removably enclosing each of said radiant heating element and said vibrator in at least one pocket.

35. A radiant therapeutic heating apparatus according to claim 1, wherein each of said at least one radiant heating elements further comprises: a layer of radiant heat generating material homogeneously impregnated with an electrically resistive material; electrically conductive tape fixed in electrical contact with the resistive material along the side; a wire adapted to apply electrical current to said conductive tapes; and a sealed flexible envelope of radiation permeable material enclosing said radiant heating element such that an electrical wire extends from the envelope to said wire.

36. A radiant therapeutic heating apparatus according to claim 35, further comprising a bag for removably enclosing said radiant heating element in a pocket.

37. A radiant therapeutic heating apparatus according to claim 36, wherein the bag is flexible and made of cloth.

38. A radiant therapeutic heating apparatus according to claim 35, further comprising: a cover having a plurality of pockets for housing each of said radiant heating elements such that each electrical wire projects from its respective pocket; a power cord adapted to supply electrical energy to each of said plurality of radiant heating elements; and a fastener adapted to close the cover wherein said power cord extends therefrom for connection to the source of electrical energy.

39. A radiant therapeutic heating apparatus according to claim 38, further comprising an enclosure adapted to at least one of enclose or integrate with said sealed radiant energy permeable envelope, said enclosure comprising at least one of: a pad; a blanket; a treatment blanket; an operative blanket adapted for use at least one of before, during or after an operation; a pillow; a bed; an animal blanket; an equine blanket; a kennel liner; a kennel; clothing; footwear; a hat; a pet bed; a warming blanket; a therapeutic support; a massaging device; a vibration device or a pad adapted to heat a portion of a body comprising at least one of a heel, ankle, planter fascia, hamstring, knee, calf, thigh, elbow, collarbone, shoulder, head, neck, temporomandibular joint, poll, wrist, back, hip, leg, foot, wither, back, spine loin, barrel, lung, sinus, respiratory system, kidney, abdomen, a muscle, limb, or joint.

40. A radiant therapeutic heating apparatus according to claim 35, further comprising a pair of electrically conductive tapes fixed in electrical contact with the resistive material along opposite sides of the radiant heat generating material.

41. A radiant therapeutic heating apparatus according to claim 35, further comprising a quick connector which connects each radiant heating element to a main power cord.

42. A radiant therapeutic heating apparatus according to claim 35, wherein a resistivity of said radiant heat generating fiberglass material provides a surface temperature for the heating apparatus, which is less than or equal to 54 degrees Celsius.

43. A radiant therapeutic heating apparatus according to claim 35, wherein the radiant heat generating material comprises fiberglass.

44. A radiant therapeutic heating apparatus according to claim 43, wherein a resistivity of said radiant heat generating fiberglass material provides a surface temperature for the heating apparatus, which is within a range of between about 44-54 degrees Celsius.

45. A radiant therapeutic heating apparatus according to claim 35, further comprising a switch for energizing the heating apparatus when electrically coupled to the source of electrical energy.

46. A radiant therapeutic heating apparatus according to claim 35, further comprising a switch adapted to activate said radiant heating element such that a surface temperature of the heating apparatus is about equal to or less than 54 degrees Celsius.

47. A radiant therapeutic heating apparatus according to claim 1, comprising a sealed radiant energy permeable envelope adapted to enclose said at least one radiant heating element, said stiffening member and said thermal insulation layer.

48. A radiant therapeutic heating apparatus according to claim 29, further comprising a switch selected from at least one of: a toggle switch; an on/off switch; a high/low switch; a rheostat; an analog switch; a digital switch; or a multiple level switch.

49. A radiant therapeutic heating apparatus according to claim 29, further comprising a switch selected from at least one of: a toggle switch; an on/off switch; a high/low switch; a rheostat; an analog switch; a digital switch; or a multiple level switch.

50. A radiant therapeutic heating apparatus of claim 29, further comprising a thermal insulation layer disposed adjacent to said stiffening member.

51. A radiant therapeutic heating apparatus according to claim 50, wherein said thermal insulation layer comprises foam insulation.

52. A radiant therapeutic heating apparatus according to claim 50, comprising a cover of a sealed radiant energy permeable envelope adapted to enclose said at least one radiant heating element, said resilient stiffener and said thermal insulation layer.

53. A radiant therapeutic heating apparatus according to claim 50, comprising a cover of a sealed radiant energy permeable envelope adapted to enclose said radiant heating elements, said stiffening member and said thermal insulation layer.

54. A radiant therapeutic heating apparatus according to claim 29, further comprising an enclosure adapted to at least one of enclose or integrate with said sealed radiant energy permeable envelope, said enclosure comprising at least one of: a pad; a blanket; a treatment blanket; an operative blanket adapted for use at least one of before, during or after an operation; a pillow; a bed; an animal blanket; an equine blanket; a kennel liner; a kennel; clothing; footwear; a hat; a pet bed; a warming blanket; a therapeutic support; a massaging device; a vibration device or a pad adapted to heat a portion of a body comprising at least one of a heel, ankle, planter fascia, hamstring, knee, calf, thigh, elbow, collarbone, shoulder, head, neck, temporomandibular joint, poll, wrist, back, hip, leg, foot, wither, back, spine loin, barrel, lung, sinus, respiratory system, kidney, abdomen, a muscle, limb, or joint.

55. A radiant therapeutic heating apparatus according to claim 29, wherein a user of the apparatus comprises at least one of: a mammal; a living being; a human; an animal; a pet; a horse; a cow; a dog; a single hump camel; a two hump camel; or a cat.

56. A radiant therapeutic heating apparatus according to claim 29, wherein said radiant heating element comprises a fiberglass material impregnated with resistive material.

57. A radiant therapeutic heating apparatus according to claim 29, further comprising resistive material adapted to provide radiant energy at wavelengths between 5 and 25 microns.

58. A radiant therapeutic heating apparatus according to claim 29, wherein a resistivity of said radiant heating element provides a surface temperature adjacent the body to be heated which is less than or equal to about 54 degrees Celsius.

59. A radiant therapeutic heating apparatus according to claim 29, wherein said radiant heating elements further comprises at least one current limiting thermostat.

60. A radiant therapeutic heating apparatus comprising: at least one radiant heating element electrically coupled to a source of electrical energy adapted to radiate energy at a wavelength which penetrates into a body; a stiffening member adapted to prevent creasing of said radiant heating element; and a covering having a pocket for housing said radiant heating element, wherein the apparatus is adapted to conform to a portion of a user's body in a therapeutic position, and wherein the portion of a user's body is a wrist and the stiffening member is curved so as to put the user's wrist in a position therapeutic position.

61. A radiant therapeutic heating apparatus according to claim 60, wherein said stiffening member is curved at about +/−5 degrees.

62. A radiant therapeutic heating apparatus according to claim 60, comprising at least one of: a control switch adapted to vary the level of radiant energy, said control switch comprising at least one of: a toggle switch; an on/off switch; a high/low switch; a rheostat; an analog switch; a digital switch; or a multiple level switch.

63. A radiant therapeutic heating apparatus comprising: at least one radiant heating element electrically coupled to a source of electrical energy adapted to radiate energy at a wavelength which penetrates into a body; a control switch adapted to vary the level of radiant energy, said control switch comprising at least one of a high/low switch or a multiple level switch; and a covering comprising two halves, each half of the cover is stitched together with stitches so as to create one or more individual pockets into which at least one heating element is inserted, wherein the apparatus is adapted to conform to a portion of a user's body in a therapeutic position.

64. A radiant therapeutic heating apparatus according to claim 63, further comprising a quick connector which connects the radiant heating element to a main power cord.

65. A radiant therapeutic heating apparatus according to claim 63, comprising a cover of a sealed radiant energy permeable envelope adapted to enclose said radiant heating element.

66. A radiant therapeutic heating apparatus according to claim 63, wherein the portion of the user's body comprises at least one of: a heel, a hamstring, an ankle, a planter fascia, a foot, a knee, a calf, a thigh, an elbow, a collarbone, temporomandibular joint, poll, a head, a neck, a shoulder, a wrist, a back, a spine, an abdomen, a hip, a leg, a wither, a loin, a barrel, a lung, a sinus, a respiratory system, a kidney, a muscle, a limb, or a joint.

67. A radiant therapeutic heating apparatus according to claim 63, further comprising resistive material adapted to provide radiant energy at wavelengths between 5 and 25 microns.

68. A radiant therapeutic heating apparatus according to claim 63, wherein a resistivity of said radiant heating element provides a surface temperature adjacent the body to be heated which is less than or equal to about 54 degrees Celsius.

69. A radiant therapeutic heating apparatus according to claim 63, wherein said radiant heating elements further comprises one or more current limiting thermostat.

* * * * *